ized tank.

United States Patent [19]

Sisbarro

[11] 4,405,489
[45] Sep. 20, 1983

[54] PRODUCTION OF A POST-FOAMING GEL AND SYSTEM THEREFOR

[75] Inventor: Frederick P. Sisbarro, Wayne, N.J.

[73] Assignee: Carter-Wallace, Inc., New York, N.Y.

[21] Appl. No.: 225,389

[22] Filed: Jan. 15, 1981

[51] Int. Cl.³ .......................... B01J 13/00; B01F 5/04; B01F 13/06
[52] U.S. Cl. .................................. 252/315.4; 53/470; 141/3; 252/90; 252/305; 252/359 E; 252/DIG. 13; 261/DIG. 26
[58] Field of Search ...................... 252/90, 305, 359 E, 252/316; 261/DIG. 26; 53/470; 141/3

[56] References Cited

U.S. PATENT DOCUMENTS

| | | | |
|---|---|---|---|
| 2,995,521 | 8/1961 | Estignard-Bluard | 252/122 X |
| 3,330,773 | 7/1967 | De Hart, Jr. | 252/305 X |
| 3,484,378 | 12/1969 | Reich et al. | 252/305 X |
| 3,541,581 | 11/1970 | Monson | 252/92 X |
| 3,705,855 | 12/1972 | Marschner | 252/90 |
| 3,728,265 | 4/1973 | Cella et al. | 252/90 |
| 3,728,276 | 4/1973 | Lieberman et al. | 252/305 |
| 3,847,571 | 11/1974 | Cole, Jr. | 261/DIG. 26 |

FOREIGN PATENT DOCUMENTS 272993 6/1927 United Kingdom ....... 261/DIG. 26

*Primary Examiner*—Richard D. Lovering
*Attorney, Agent, or Firm*—Elliot M. Olstein; Louis E. Marn

[57] ABSTRACT

A stable post foaming gel suitable for producing lathers for shaving, shampooing and other personal care use is formed for packaging in a continuous closed system by passing the post foaming gel components through a pressurized tank to a filling machine for introducing the formed post-foaming gel into a suitable package or container, with the system being pressurized by the pressurized tank.

26 Claims, 2 Drawing Figures

PRODUCTION OF A POST-FOAMING GEL AND SYSTEM THEREFOR

The present invention relates to post-foaming gels, and in particular post-foaming gels which are suitable for personal care preparations employed to produce lathers for shaving, shampooing and the like.

U.S. Pat. No. 2,995,521 discloses a foam producing composition in the form of a post-foaming gel, which is comprised of an aqueous soap ingredient and a post-foaming agent.

U.S. Pat. No. 3,541,581 discloses a post-foaming gel, which is comprised of an aqueous soap ingredient, a post-foaming agent and a water soluble gelling agent, with the patent indicating that such gelling agent is required to provide a stable post-foaming gel.

The present invention is directed to an improved process and apparatus for the production of a stable post-foaming gel for packaging, and to the improved stable post-foaming gel produced thereby.

In accordance with the present invention, there is provided an improvement in a post-foaming gel by producing the post-foaming gel by an improved process and in an improved system.

The post-foaming gel is continuously produced by separately metering an aqueous soap ingredient and a post-foaming agent into admixture with each other, intimately mixing the post-foaming agent and soap ingredient and passing the mixture to a filling machine for introduction into a package or container. Such steps are effected in a continuous flow system under pressure, with the mixture being maintained in the flow system for a time and at a temperature and pressure sufficient to produce a post-foaming gel prior to the filling machine. The system pressure is preferably maintained by the use of a pressurized tank, with the mixture being passed through the tank to the filling machine.

More particularly, in accordance with the present invention, the aqueous soap ingredient and the post-foaming agent are continuously separately metered and mixed in a closed system, with the resulting mixture then being passed through a pressurized tank to the filling machine, with the conditions in the closed pressurized system being controlled to provide for the production of the post-foaming gel and filling thereof at appropriate filling rates, without prefoaming in the system, and to provide in the package or container a stable post-foaming gel having improved properties.

The system for continuously producing the post-foaming gel includes as principal components: a first pump means for the aqueous soap ingredient, a second pump means for the post foaming agent; a mixing means; means for pressurizing the system; a filling means for introducing the formed post-foaming gel into a suitable package or container, with such components being interconnected such that the aqueous soap ingredient and post-foaming agent are admixed with each other under pressure, and passed to the filling means. In accordance with a preferred embodiment, the means for pressurizing the system is comprised of a pressurized tank, with the mixture being passed through the pressurized tank to the filling means.

As known in the art, one component of the post-foaming gel is the aqueous soap ingredient, with such soap ingredient being either a soap or a surface active agent, usually called a wetting agent, which is generally anionic or nonionic in character, with the soap ingredient preferably being a soap.

The soaps (water soluble salts of higher fatty acids) which are amine or basic salts, suitable for the production of a post-foaming gel are generally known in the art. In general, such a component is an alkali, ammonium or soluble amine salt of a fatty acid such as stearic acid, palmitic acid, myristic acid and the like. As known in the art, soaps may also be prepared by neutralization or saponification of animal fats, such as tallow or vegetable fats. The selection of a suitable soap component is deemed to be within the scope of those skilled in the art from the teachings herein.

The anionic or nonionic surface active agent which can be employed instead of a soap, or in conjunction therewith, should be one which is appreciably soluble in water, and as examples of such agents there may be mentioned triethanolamine lauryl sulfate, sodium lauryl sulfate, sodium dodecyl benzene sulfonate, water-soluble polyoxyethylene ethers of alkyl-substituted phenols and water-soluble polyoxyethylene cetyl ethers. The selection of a suitable wetting agent is deemed to be within the scope of those skilled in the art from the teachings herein.

The other principle ingredient of the post-foaming gel is a post-foaming agent, which as generally known in the art is an organic liquid having a vapor pressure from about 6 to about 30 psig at a temperature from about 90° to 100° F. Such post-foaming agents include saturated aliphatic hydrocarbons having from 4 to 6 carbon atoms, such as butanes, preferably N-butane, pentanes and hexanes and partially or wholly halogenated hydrocarbons such as trichlorotrifluoroethane, 1,2-dichloro, 1,1,2,2-tetrafluoroethane, and the like. Mixtures of these hydrocarbons and/or halogenated hydrocarbons can be employed for providing a desired vapor pressure.

The aqueous soap ingredient, and the post-foaming agent are the principle ingredients in the production of a post-foaming gel suitable for personal care use, which is produced in accordance with the present invention.

The post-foaming gel produced in accordance with the present invention may also include a gelling aid as described in U.S. Pat. No. 3,541,581. As disclosed in such patent, such gelling aids are water-soluble derivatives of naturally occurring substances such as cellulose, sucrose and glucose. Although such gelling aids may be included as an ingredient for the production of a post-foaming gel in accordance with the invention, such gelling aid is not required for the production of a post-foaming gel, and as a result, need not be included as an ingredient.

The post-foaming gel may also include other miscellaneous additives or ingredients such as humectants, foam supplements, perfumes, skin conditioners, emollients, and the like.

In accordance with a particularly preferred embodiment, the present invention is directed to the production of a post-foaming gel from a composition which does not include a gelling agent, and which is basically comprised of an aqueous soap ingredient, a post-foaming agent and an oil which is sparingly soluble in water, which is either an oily hydrocarbon (one that is not normally volatile at room temperature), and/or a liquid fatty alcohol and/or a fatty ester.

In formulating a post-foaming gel for production in accordance with the invention, in general, the post foaming gel is comprised of from about 40 to about 90% water, from about 4 to about 25% of the soap ingredient, which is either a soap or wetting agent, preferably a soap, and from 0.5 to 12% of the post-foaming agent. If a gelling aid is employed, such gelling aid is generally employed in an amount of from 0.01 to 5%. All percentages are by weight.

In accordance with the preferred embodiment wherein the principal ingredients of the post-foaming gel are comprised of water, a soap ingredient, a post-foaming agent and an oil, the water is employed in an amount from about 40 to about 80%, the soap ingredient in an amount of from about 10 to 25%, the post-foaming agent in an amount of from about 1.5 to 4% and the oil in an amount of from about 0.25% to 1.5%, all by weight.

BRIEF DESCRIPTION OF DRAWINGS

The invention will be further described with respect to the accompanying drawings, wherein.

Figures 1, 2:
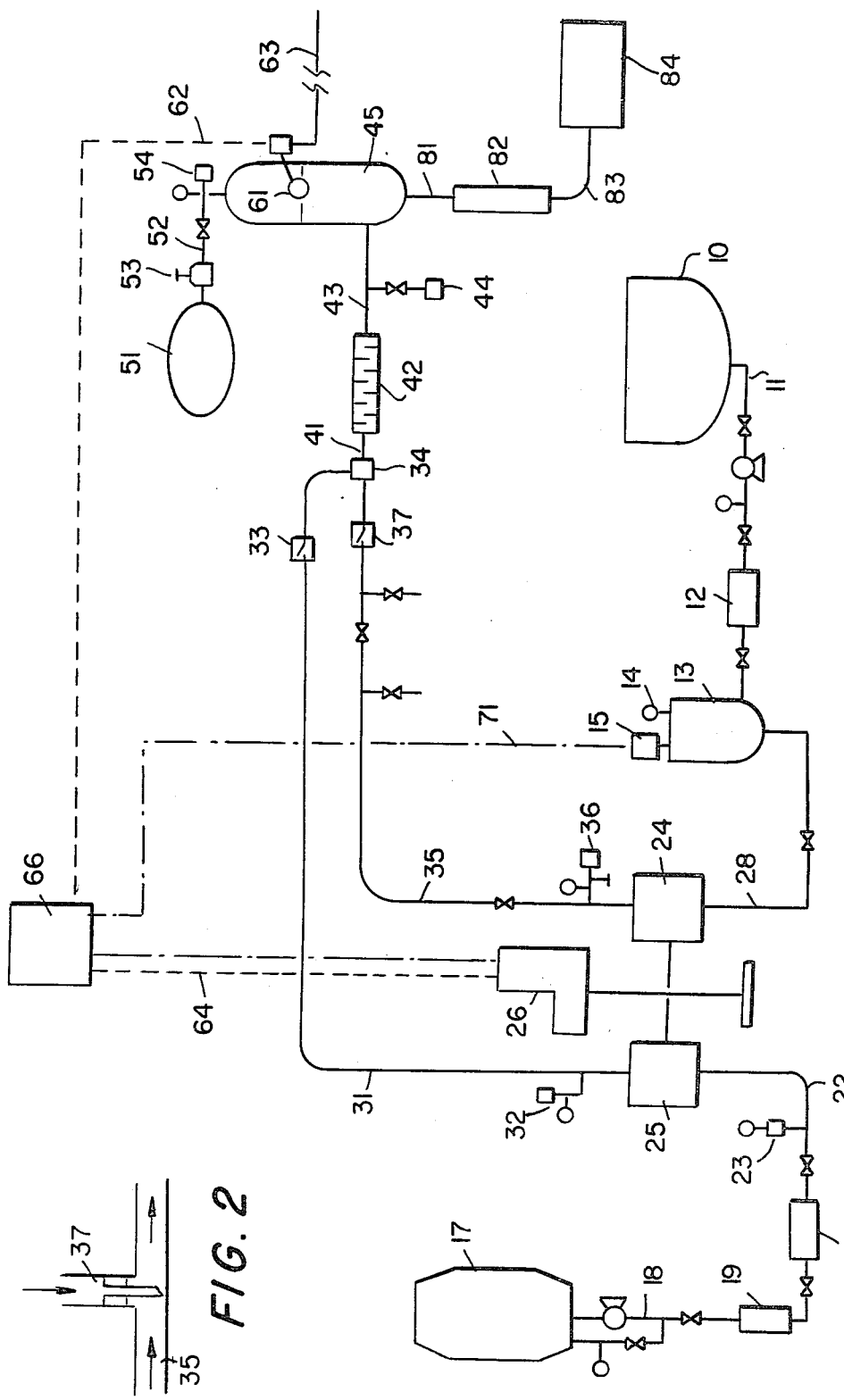
FIG. 1 is a simplified schematic flow diagram of an embodiment of the system for producing a post-foaming gel in accordance with the present invention.
FIG. 2 is a simplified schematic detailed representation of a portion of the embodiment of FIG. 1.

It is to be understood the invention described with respect to the drawings is for purposes of illustration only, and the invention is not to be limited to the particular embodiment shown in such drawings. Moreover, it is to be understood that various equipments such as valves, controllers and the like have not been completely shown, and the placing of appropriate equipment at appropriate places is within the scope of those skilled in the art.

Referring now to the drawing, the aqueous soap ingredient of the post-foaming gel is maintained in a storage tank. Such aqueous soap ingredient may include other components to be included in the composition, such as hereinabove described, except that such aqueous soap ingredient does not include the post-foaming agent. In the case where the post-foaming gel is to be formulated in accordance with the preferred embodiment, which further includes an oil, such oil is present in the soap ingredient maintained in the storage tank. If the gelling aid is to be employed, such gelling aid is also present with the aqueous soap ingredient.

The aqueous soap ingredient in supply tank 10 is fed therefrom through line 11, including appropriate valves and pumps, as schematically shown, through a strainer 12 and into a surge vessel, schematically generally indicated as 13. The surge vessel 13 functions to provide a constant non-pulsing supply source for the aqueous soap ingredient of the composition, and is provided with a pressure gauge 14 and a low level probe 15, of a type known in the art, which functions to shut down the entire system when the amount of material in vessel 13 falls below a certain level.

The post-foaming agent is stored in a suitable supply tank 17 and is fed to the system through line 18, which includes suitable pumps and valves, as schematically represented, through a suitable adsorbant, such as a molecular sieve, schematically represented as 19, and a suitable filter or similar separation device for removing particulate matter, and schematically generally indicated as 21. The outlet 22 from filter 21 is provided with a suitable pressure relief valve, schematically generally indicated as 23.

The system is provided with means for separately metering the aqueous soap ingredient and the post foaming agent in the form of two metering or proportioning pumps 24 and 25, which as particularly shown contain a single drive mechanism 26. It is to be understood, however, that the pumps 24 and 25 may each have their own drive mechanisms.

The pump 24 is provided with the aqueous soap ingredient through line 28, and the pump 25 is provided with post-foaming agent through line 22.

The metering pumps 24 and 25 are set and operated in a manner such that they provide a constant ratio of post-foaming agent to aqueous soap ingredient, in the respective outlet lines thereof, irrespective of the outflow rate of the pumps. Thus, the output rates of pumps 24 and 25 may be proportionally changed; i.e., the ratio of post-foaming agent to aqueous soap ingredient remains constant.

The post-foaming agent is pumped by pump 25 through suitable fluid flow means for subsequent admixture with the aqueous soap ingredient. As shown, the post-foaming agent is pumped through line 31 which includes a combination pressure relief valve and pulsation dampener, schematically generally indicated as 32, and a check valve 33, and is provided therefrom to an injection device, schematically generally indicated as 34, for introducing the post-foaming agent into the flowing aqueous soap ingredient.

The aqueous soap ingredient is pumped by pump 24 through suitable flow means for introduction into a mixing means after admixture with the post-foaming agent. As shown, the aqueous soap ingredient flows through line 35, which includes a pressure relief valve, schematically generally indicated as 36, and a check valve 37, and the post-foaming agent is introduced into the flowing aqueous soap ingredient by means of the injection device 34.

As shown more particularly in FIG. 2, the post-foaming agent flows into a nozzle-like element 37, which is inserted into the middle of the flowing aqueous soap ingredient in line 35. Thus, the flowing post-foaming agent in line 31 is continuously introduced into the flowing aqueous soap ingredient in line 35 by use of an injection-like nozzle 37.

It is to be understood, however, that although the use of such an injection device is preferred, such use is not required. Thus, the flowing post foaming agent can be continuously introduced into the stream of flowing aqueous soap ingredient by use of a "T" type of juncture, instead of an injection nozzle, although the use of such injection nozzle is preferred.

The combined post-foaming agent and aqueous soap ingredient, in line 41 then flows through an in-line static mixer, schematically generally indicated as 42 for accomplishing intimate mixing of the post-foaming agent and aqueous soap ingredient. Although a static mixer is preferred, it is to be understood that other types of mixers could also be employed; e.g., a mechanical mixer.

The intimate mixture of post-foaming agent and aqueous soap ingredient flows from mixer 42 through line 43, which includes a pressure relief valve schematically generally indicated as 44, and is introduced into a pressurized tank, generally indicated as 45.

The pressurized tank 45 serves the purpose of pressurizing the system to the desired system operating pressure, and further provides a decrease in the velocity and residence time of the materials in the system (in the case where a gelling aid is not employed), to provide for production of the post-foaming gel. In the case where a gelling aid is employed, in most cases, the change in velocity and/or residence time is not required for formation of such gel. As hereinafter described, the pressurized tank 45 also functions as a flow controller.

A suitable gas, preferably an inert gas, such as nitrogen, is provided from a gas supply tank 51 to tank 45 through line 52, which includes a suitable pressure regulator, schematically generally indicated as 53 and a pressure relief valve, schematically generally indicated as 54. Although an inert gas is preferred, it is to be understood, that in some cases oxygen could also be employed as the gas for pressurizing tank 45. As should be apparent, oxygen or air is generally not preferred in view of the presence of a hydrocarbon in the system.

The gas provided to tank 45 functions to pressurize tank 45 to the desired operating pressure of the system, and tank 45 therefore functions to pressurize the system to the desired operating pressure.

The pressurized vessel or tank 45 is also provided with a suitable control mechanism which controls motor 26 of the pumps 24 and 25 to thereby change the output flow rate of the pumps in response to changes in the level of material in tank 45. Thus, for example, a suitable level controller, such as a control float ball 61 may be placed within tank 45, with the control ball 61 operating in response to liquid levels in tank 45 to proportionally change the output pressure 62 of control air provided through line 63. The output air signal in line 62 is provided to a suitable control box, schematically indicated as 66, which in turn provides a control air signal through automatic control line 64 to the pump motor 26 to control the motor speed, which in turn controls the output flow rate from the pumps 24 and 25. Such control air functions to change and control the operation of the pumps from an off position to a maximum supply rate, and at various output rates therebetween. As previously indicated, although the output rate of the pumps 24 and 25 are changed in response to levels in pressurized tank 45, such rates are changed proportionally so that the ratio of post-foaming agent to aqueous soap ingredient remains constant.

It is to be understood that although the control has been described with respect to pneumatic signals, other control signals could also be employed within the spirit and scope of the invention; for example, electrical controls. Similarly, although the level controller has been shown in the form of a control float ball, other types of controls could be used, such as an ultrasonic probe or the like.

The pump motor 26 is also controlled in response to the low level probe 15 for tank 13, by means of an electrical signal in line 71 provided to control box 66. The probe 15 functions to shut off the pumps 24 and 25 when the aqueous soap ingredient falls below a certain level in tank 13.

The intimate mixture of post-foaming agent and aqueous soap ingredient is formed into a post-foaming gel prior to being passed from the gas pressurized tank to a filling machine through suitable fluid flow means. In accordance with the illustrated embodiment, the pressurized tank 45 is provided with a plurality of outlet lines 81 (only one of which is shown) through which the post-foaming gel is withdrawn from the pressurized tank 45 and passed through a heat exchanger 82 to control the temperature thereof to a value at which the gel can be filled without "blooming." The temperature is regulated in heat exchanger 82 to a value at which proper flow can be maintained, without prefoaming or "blooming" of the gel, and the gel withdrawn from the heat exchanger 82 in line 83 is provided to an appropriate filling machine, schematically designated as 84 for introducing the gel into a suitable package therefor, such as a container.

In accordance with the system, the pressure which is maintained in the system by pressurized tank 45 is coordinated with the operating temperature and residence time of the mixed aqueous soap ingredient and post-foaming agent in the system, such that the intimate mixture of post-foaming agent and aqueous soap ingredient is in the form of a gel upon being withdrawn from pressurized tank 45, and is maintained as a post-foaming gel capable of continuously flowing through the system for introduction into a container or package at an appropriate filling rate.

In general, the system pressure is regulated to a value in the order of from 10 to 100 psig, preferably 30 to 50 psig and the temperature is maintained so that the post-foaming gel is packaged at a temperature in the order of from 0° to 100° C., and preferably from 5° to 20° C. It is to be understod that the pressure and temperature are coordinated so as to enable formation of the post-forming gel in the system, while preventing the gel from having too thick or too thin of a consistency so as to enable proper filling thereof. The selection of optimum temperatures and pressures should be apparent to those skilled in the art from the teachings herein.

In order to help in maintaining proper temperatures various lines and/or equipment may be equipped with suitable means for providing temperature control such as insulation, cooling coils and the like.

In accordance with the hereinabove described system, the post-foaming agent and aqueous soap ingredient are continuously mixed and formed into a gel, with the system being pressurized between the outlet of the pumps and the filling machine by the pressurized tank. In addition, in accordance with the system, the post-foaming agent and the aqueous soap ingredient are mixed under pressure, and maintained under pressure for proper introduction into a container or package by means of a conventional filling machine. The continuous mixing or metered amounts of soap ingredient and post-foaming agent under pressure provides an improved post-foaming gel. Although the specific embodiment provides for pressurization of the system from the outlet of the metering pumps to the filling machine, it is to be understood that the system could also be operated in a manner such that the system is pressurized in only the portion thereof from the mixing of the components of the filling machine. Similarly, although the system employs a pressurized tank, the system could be pressurized in another manner, although a pressurized tank, as described, is particularly preferred in that it reduces overall costs and provides an easier design.

In accordance with the present invention, there is provided for continuous production of a post-foaming gel, with the components being mixed and maintained under pressure, in a closed system, and with minimum contact with gas (the only gas contact is in the pressurized tank 45, which is only a brief contact with a flowing system). Applicant has found that by employing such a system, there is provided an improvement in the production of post-foaming gels, as evidenced by improved properties of such post-foaming gels. In particular, the post-foaming gel has improved stability (little or no change in the physical state or properties thereof over time), and improved post-foaming characteristics as evidenced by non-foaming over longer periods of time, in the absence of application of friction. In addition, there is provided a more intimate mixture of the post-foaming agent and aqueous soap ingredient as evidenced by improved clarity of the post-foaming gel.

Furthermore, in accordance with the system, pre-foaming of the gel, prior to filling thereof into a suitable package or container is avoided, while maintaining proper flow properties and filling characteristics to enable filling of a package or container at an appropriate rate.

In addition, the procedure is a safer process in that it is no longer necessary to mix large batches of the post-foaming agent, which is generally a flammable component in that only small amounts of such post-foaming agent are metered into the flowing aqueous soap ingredient at any time.

These and other advantages should be apparent to those skilled in the art from the teachings herein.

The above system has been employed in a demonstration unit for the production of a post foaming gel in which the aqueous soap ingredient is maintained in the storage tank at about 10° to 20° C., and the post-foaming agent is maintained in the storage tank at about ambient conditions. The system is operated at 50 psig by the use of nitrogen, and the temperature is maintained in the system to provide for filling of 7 oz. cans at a temperature of from 10° to 16° C. In such a system, the production rate, employing two outlet lines from the pressurized tank was from 60 to 90 cans per minute for a 7 oz. fill rate.

The post-foaming gel which was filled in the system included as principle components, water (about 75% by weight), acetylated lanolin alcohol (about 1% by weight), a mixture of palmitic and myristic acid in a total amount of about 10% by weight; diethanolamine in an amount of about 3% by weight and a post-foaming agent comprised of isopentane and isobutane in a total amount of about 2.6% by weight.

The post-foaming gel was effectively formed without a gelling aid, and remained as a gel, if left undisturbed, for at least 30 seconds and foams up within 5 seconds when rubbed in a hand.

Numerous modifications and variations of the present invention are possible in light of the above teachings and, therefore, within the scope of the appended claims, the invention may be practiced otherwise than as particularly described.

I claim:

1. A process for continuously producing a post-foaming gel for packaging thereof comprising:
admixing separately metered amounts of an aqueous soap ingredient and a post-foaming agent to form an intimate mixture thereof; passing said mixture to a filling machine for packaging the gel, said steps being effected in a continuous flow system under pressure, said mixture being maintained within the continuous flow system for a time and at a pressure and temperature sufficient to produce a post-foaming gel capable of continuously flowing through the system to the filling machine for packaging thereof.

2. The process of claim 1 wherein the mixture is free of a gelling agent.

3. The process of claim 1 wherein the mixture is comprised of from 40% to 80% water, from 10% to 25% of soap ingredient, from 1.5% to 4% of post-foaming agent, and from 0.25% to 1.5% of oil, all by weight.

4. The process of claim 1 wherein the mixture is passed through a pressurized tank to a filling machine, said pressurized tank maintaining the pressure for said system.

5. The process of claim 4 wherein the pressurized tank is pressurized by introduction of pressurized gas.

6. The process of claim 5 wherein the pressurized tank maintains a pressure of from 10 to 100 psig.

7. The process of claim 6 wherein said pressure is from 20 to 50 psig.

8. The process of claim 5 wherein the post-foaming gel is formed prior to withdrawing the mixture from the pressurized tank.

9. The process of claim 8 wherein the mixture is free of a gelling aid.

10. The process of claim 5 wherein the gas introduced into the pressurized tank is an inert gas.

11. The process of claim 10 wherein the mixture is comprised of from 40 to 90% water, 4 to 25% soap ingredient and 0.5 to 12% post-foaming agent, all by weight.

12. The process of claim 5 wherein the continuous flow system under pressure is a closed system and said system is maintained free of air.

13. The process of claim 5 and further comprising:
varying the flow of each of the separately metered aqueous soap ingredient and post-forming agent in response to levels in the pressurized tank.

14. The process of claim 13 wherein the ratio of separately metered amounts of aqueous soap ingredient and post-foaming agent is maintained constant as the flow is varied in response to levels in the pressurized tank.

15. The process of claim 14 wherein the mixture is comprised of from 40% to 80% water, from 10% to 25% of soap ingredient, from 1.5% to 4% of post-foaming agent, and from 0.25% to 1.5% of oil, all by weight.

16. The process of claim 5 and further comprising:
controlling the temperature of the formed post-foaming gel to prevent pre-foaming thereof by passing the formed post-foaming gel through a heat exchanger located between the pressurized tank and a filling machine.

17. The process of claim 1 wherein the aqueous soap ingredient is comprised of water, soap ingredient and an oil.

18. The process of claim 17 wherein the oil is sparingly soluble in water and is at least one member selected from the group consisting of oily hydrocarbons, liquid fatty alcohols and liquid fatty esters.

19. The process of claim 5 and further comprising:
packaging the formed post-foaming gel in a filling machine at a temperature from 0° C. to 100° C.

20. A system for continuously producing a post-foaming gel for packaging thereof, comprising:
a supply means for an aqueous soap ingredient; a supply means for a post-foaming agent, a first metering means for metering an aqueous soap ingredient from the supply means therefor; a second metering means for metering a post-foaming agent from the supply means therefor; mixing means; a pressurized tank; filling means for introducing a post-foaming gel into a package therefor; first fluid flow means for connecting the first metering means to said mixing means; second fluid flow means for connecting the second metering means with the first fluid flow means to mix the aqueous soap ingredient with the post-foaming agent for mixing in the mixing means; third fluid flow means connecting the mixing means with the pressurized tank; fourth fluid flow means connecting the pressurized tank with the filling means whereby the mixture of aqueous soap ingredient and post-foaming agent flows to the filling means through the pressurized tank and is formed into a post-foaming gel prior to the filling means; a supply tank for pressurized gas; and means for introducing pressurized gas from the supply tank into the pressurized tank to pressurize the pressurized tank and at least the portion of the system from the mixing means to the filling means.

21. The system of claim 20 wherein the mixing means is a static mixer.

22. The system of claim 20 wherein the first and second fluid flow means are connected through an injection nozzle.

23. The system of claim 20 and further comprising: control means connected to the pressurized tank and the first and second metering means for controlling the output of the first and second metering means to vary the flow rate in response to levels in the pressurized tank.

24. The system of claim 23 wherein said control means and the first and second metering means maintain a constant ratio of the metered aqueous soap ingredient and metered post-foaming agent as flow rates are varied in response to levels in the pressurized tank.

25. A system for continuously producing a post-foaming gel for packaging thereof, comprising:
a supply means for an aqueous soap ingredient; a supply means for a post-foaming agent; a first metering means for metering an aqueous soap ingredient from the supply means therefor; a second metering means for metering a post-foaming agent from the supply means therefor; mixing means; means for pressurizing the system; a tank; filling means for introducing a post-foaming gel into a package therefor; first fluid flow means for connecting the first metering means to said mixing means; second flow means for connecting the second metering means with the first fluid flow means to mix the aqueous soap ingredient with the post-foaming agent for mixing in the mixing means; third fluid flow means connecting the mixing means with the tank; fourth fluid flow means connecting the tank with the filling means whereby the mixture of aqueous soap ingredient and post-foaming agent flows to the filling means through the tank and is formed into a post-foaming gel prior to the filling means; a control means operatively connected to the tank and the first and second metering means to control the output of the first and second metering means and vary flow rates in response to levels in the tank.

26. The system of claim 25 wherein the first and second metering means and the control means maintain a constant ratio of the metered amount of aqueous soap ingredient and post-foaming agent as the flow rates thereof vary.

* * * * *